United States Patent [19]

Greenhouse

[11] 4,275,628
[45] Jun. 30, 1981

[54] SYRINGE AND NEEDLE DESTROYER

[76] Inventor: Hyman D. Greenhouse, Cranbury Post Office, Main St., Cranbury, N.J. 08512

[21] Appl. No.: 89,914

[22] Filed: Oct. 31, 1979

[51] Int. Cl.³ .......................... B26D 5/10; B23D 15/00
[52] U.S. Cl. ........................................ 83/167; 83/580; 83/622; 83/629; 83/925 R
[58] Field of Search ............. 83/167, 580, 599, 925 R, 83/620, 622, 629; 225/103

[56] References Cited
U.S. PATENT DOCUMENTS

| 3,404,593 | 10/1968 | Arcarese et al. | 83/925 R |
|---|---|---|---|
| 3,469,750 | 9/1969 | Vanderbeck | 83/925 R |
| 3,736,824 | 6/1973 | Dunnican | 83/925 R |
| 3,785,233 | 1/1974 | Robinson | 83/167 |
| 4,035,911 | 7/1977 | Nethercutt | 83/167 X |

*Primary Examiner*—J. M. Meister
*Attorney, Agent, or Firm*—Lackenbach, Lilling & Siegel

[57] ABSTRACT

A device is disclosed for severing both a needle portion and an end nub portion of a syringe. The device includes a receptacle for the cutoff portions and a removable cover. A horizontally movable severing means may be suspended from the undersurface of the cover. Mounted on the cover is a handle which is mechanically linked to the severing means. Actuation or movement of the handle thereby causes horizontal movement of the severing means. By resting the syringe in a shoulder portion of the cover, the needle and nub portions of the syringe extend downward through an opening and are in line with the severing means. Therefore, when the severing means is moved in a horizontal direction, it will necessarily cut off the needle and nub portions.

3 Claims, 10 Drawing Figures

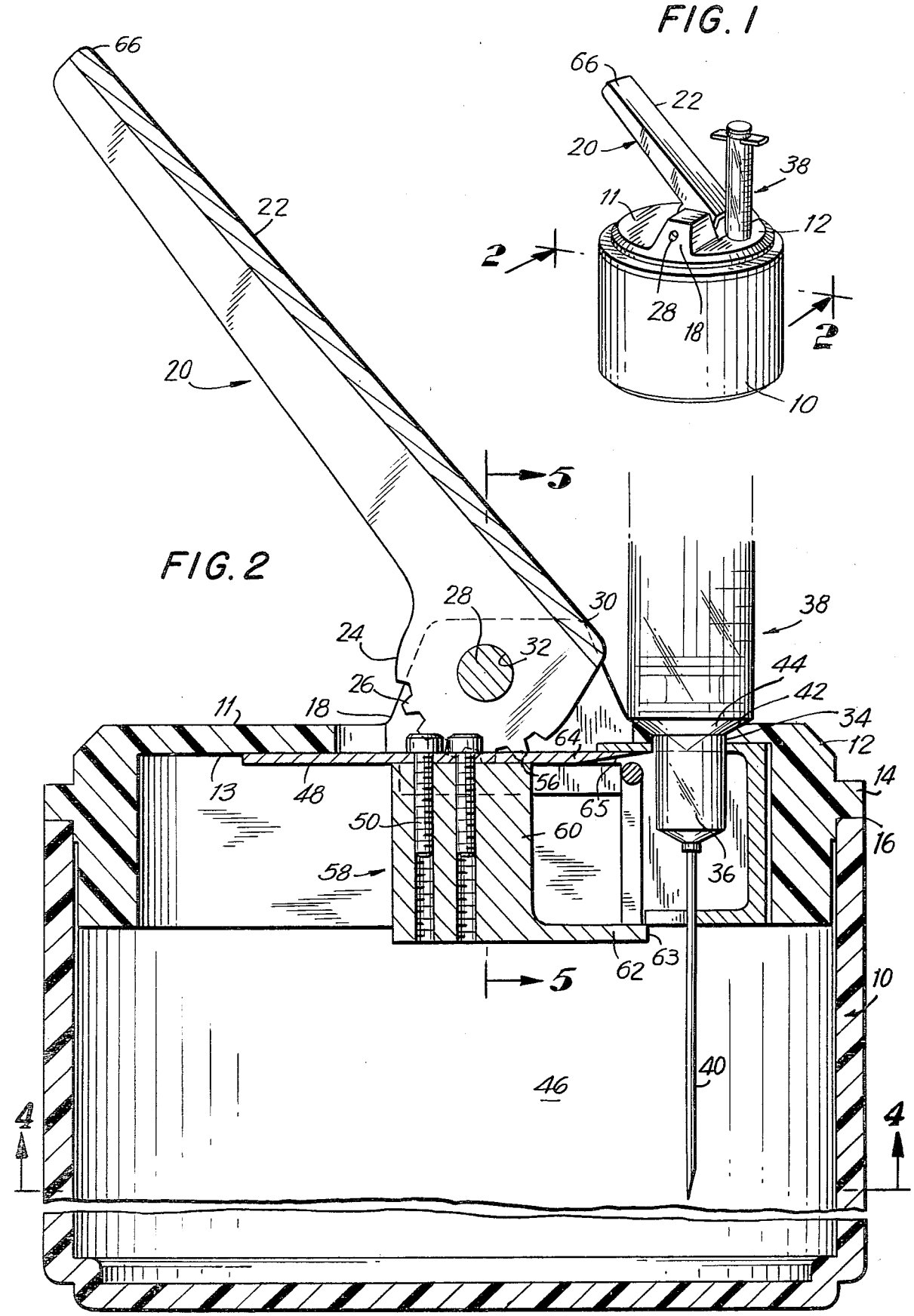

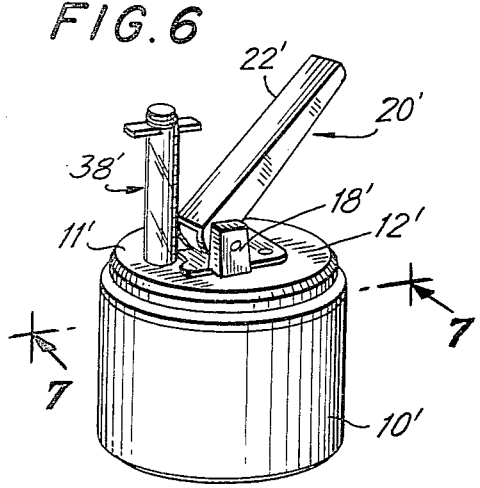
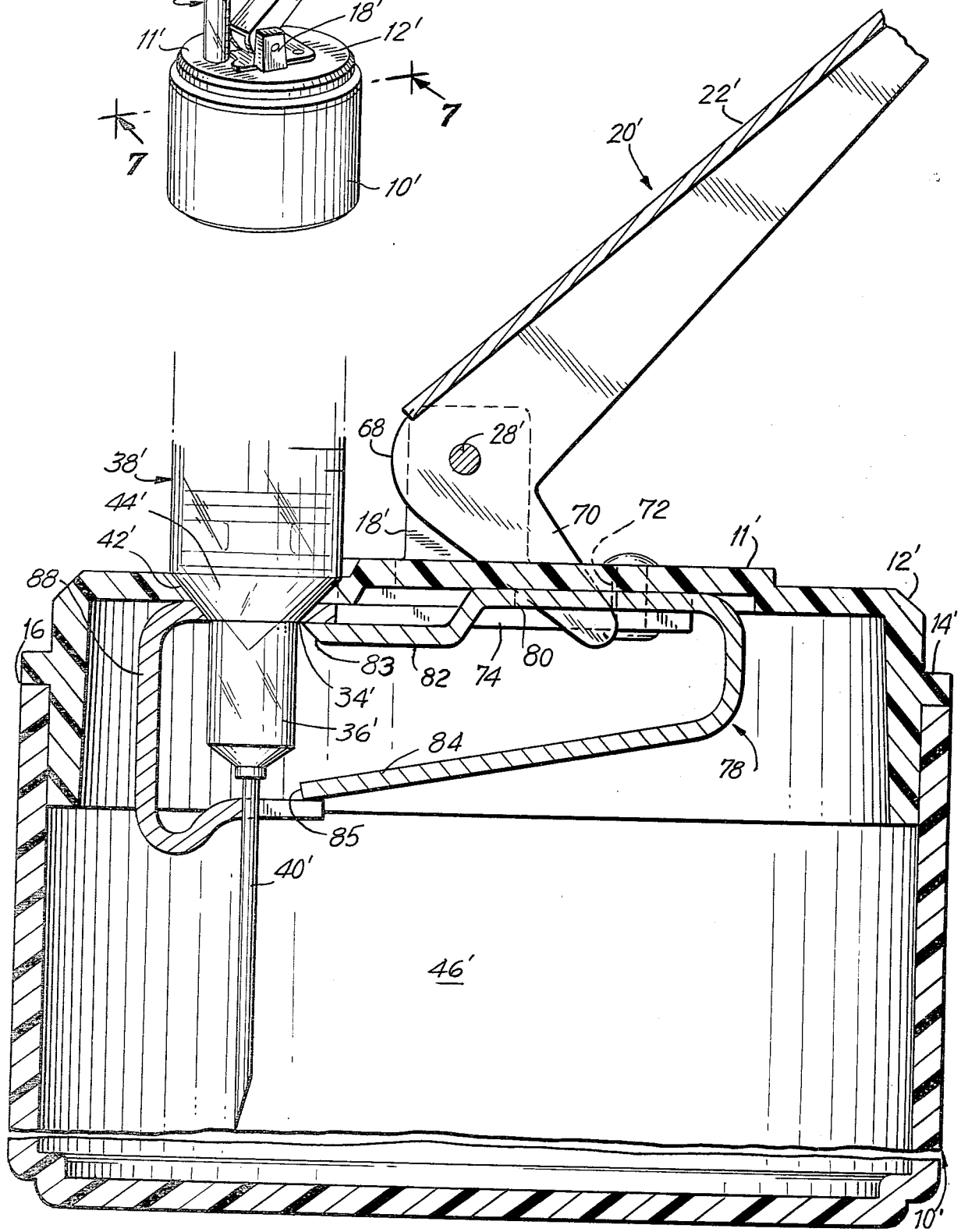

SYRINGE AND NEEDLE DESTROYER

FIELD OF THE INVENTION

For various health reasons, such as prevention of the spread of disease, it is important that a hypodermic needle be destroyed after its use. By such destruction it is impossible to re-use the hypodermic needle and to spread germs or infectious diseases. Moreover, there are several laws which require doctors and nurses to destroy hypodermic needles immediately after use. Furthermore, destruction of the syringe and needle renders them useless to drug addicts who might otherwise steal used syringes.

This invention relates to a device designed for destroying both the hypodermic needle and the hypodermic syringe portion. By doing this it becomes impossible to re-use either the hypodermic syringe or the hypodermic needle and the spread of infectious diseases and germs is effectively checked.

DESCRIPTION OF THE PRIOR ART

Known in the art are various hypodermic needles which include means for destroying the needle after its use; however, none of these devices include any means for destroying the hypodermic syringe portion itself.

Dunnican (U.S. Pat. No. 3,736,824) discloses a portable device for destroying hypodermic needles. This device uses a lever arm with a cutting blade to sheer the cannula off at a point close to the syringe. A basic disadvantage of this device is that it does not provide for destruction of the syringe, in addition to the cannula.

Dick (U.S. Pat. No. 3,796,359) discloses a different device for destroying hypodermic needles. In this device a sheath is provided which has a longitudinal channel constructed with a diaphragm. After use, the needle is inserted into the channel in the sheath as far as it will go. Then, the syringe is rotated and, because of the action of the diaphragm, the needle is snapped off. A disadvantage of this device is that it is not an efficient way to break the needle. For instance, it will require a great deal of bending the syringe back and forth and rotating it before the needle will actually be snapped off and be rendered unusable. In addition, this device cannot provide for destruction of the syringe.

Koenig (U.S. Pat. No. 3,893,608) discloses still another method of destroying hypodermic needles. A major disadvantage of this device is that it is extremely complex and difficult to use. Basically, the hypodermic needle is destroyed by bending back and forth until finally it breaks off from the syringe. Further, this device does not include any provision for destroying the syringe portion.

SUMMARY OF THE INVENTION

Therefore, it is an object of this invention to provide a simple and compact device which is capable of destroying both the hypodermic needle and the hypodermic syringe quickly and simply in a one-step operation.

This is accomplished by a device which includes a receptacle with a removable cover. Suspended from the cover is a horizontally movable severing means. Mounted on the cover is a handle mechanically linked to the severing means. By actuating or moving the handle the severing means is caused to move in a horizontal plane. An aperture is provided in the cover so that the needle and a nub portion of the syringe can pass through the aperture and the remaining portion of the syringe can rest on the cover. Thus, when the severing means is moved in a horizontal plane, it will cut off both the needle and the nub portion of the syringe extending downward from the cover. The cutoff portions then drop into the receptacle and the entire hypodermic syringe and needle are rendered totally useless.

BRIEF DESCRIPTION OF THE DRAWINGS

FIG. 1 is a perspective view of one embodiment of the apparatus of this invention, showing the hypodermic needle in position for insertion into the unit for simultaneous destruction of the nub and needle portions;

FIG. 2 is a cross-sectional view taken substantially along the line 2—2 of FIG. 1, showing the hypodermic needle and the nub portion of the syringe in position for destruction;

FIG. 6 is a perspective view of a second embodiment of the invention, showing the hypodermic needle in position for insertion into the unit for simultaneous destruction of the nub and needle portions;

FIG. 7 is a cross-sectional view taken substantially along the line 7—7 of FIG. 6, showing the hypodermic needle and the nub portion of the syringe in position for destruction;

DETAILED DESCRIPTION OF THE INVENTION

Figure 3:
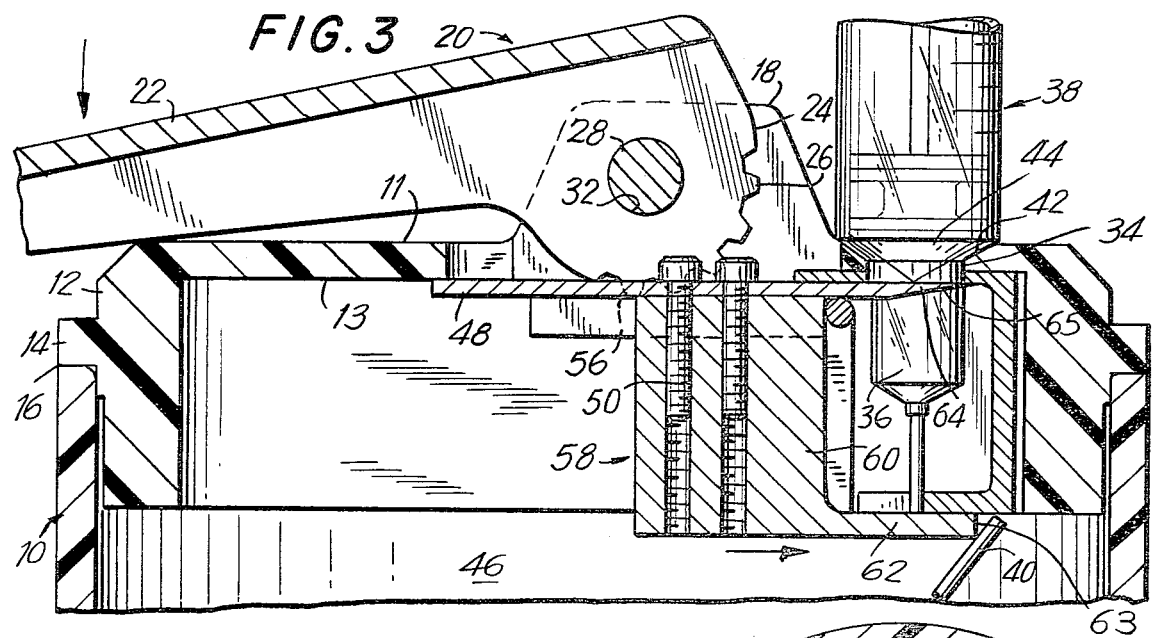
FIG. 3 is a view similar to that of FIG. 2, but showing only the top portion of the device, and showing the device after the blade means have cut off the needle and the nub portion of the syringe.
Figure 4:
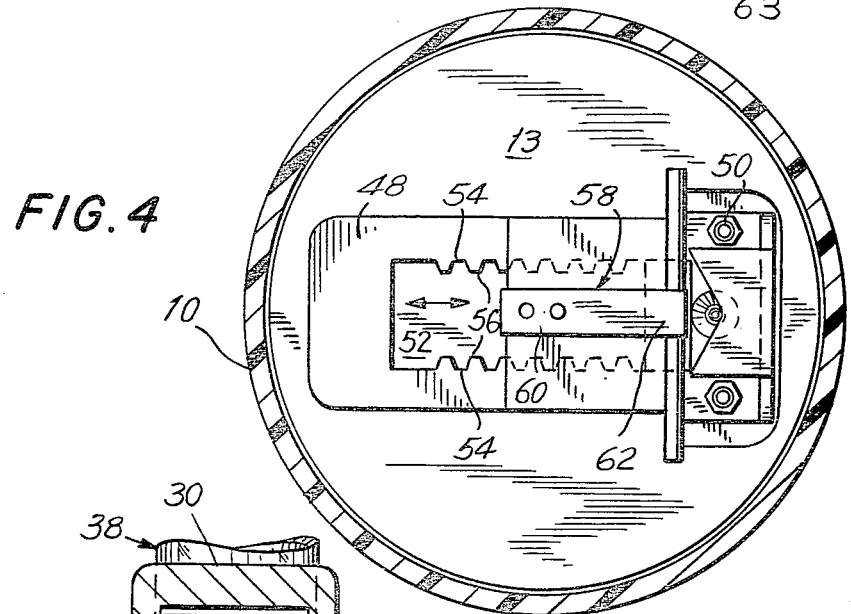
FIG. 4 is a cross-sectional view taken substantially along the line 4—4 of FIG. 2, showing the underside of the cover of the apparatus.

This invention includes the provision of a horizontally movable severing means, which is mechanically linked to an actuating handle. By actuating or moving the handle of the device, the mechanical link causes the severing means to move in a horizontal plane. This movement of the severing means causes cutting surfaces to come in contact with the needle and the nub portion of the syringe and causes them to be cut off.

Shown in this application are just two embodiments of this invention. It must be appreciated that there are many other ways to mechanically link the horizontally movable severing means and the actuating handle. In each of the embodiments shown in this application, the basic supporting structures are similar. Both embodiments include a receptacle with a cover and supporting members for the handle. Therefore, these portions of the device will be described once, but such description is applicable to both embodiments.

Referring now to the drawings wherein two embodiments of the invention are illustrated, the combination syringe and needle destroyer includes a receptacle 10 (10'). The receptacle 10 (10') may be made of any suitable material and formed in any desired shape. In the preferred embodiments, shown in FIGS. 1 and 6, the receptacle is essentially in the shape of a round jar or the like. Fitted onto the receptacle is a cover 12 (12'). Preferably, the shape of the cover 12 (12') corresponds to that of the receptacle 10 (10') so that they may be removable fitted together to obtain a closed receptacle. As best shown in FIGS. 2 and 7, the exterior diameter of the cover 12 (12') is approximately equal to the interior diameter of the receptacle 10 (10'). Extending outward from and formed along the entire periphery of the cover 12 (12') is a flange or shoulder portion 14 (14'). Thus, to fit the cover 12 (12') onto the receptacle 10 (10') the cover is inserted into the central orifice portion of the receptacle 10 (10') until the shoulder 14 (14') abuts against the top surface 16 (16') of the receptacle 10 (10'). In this manner, the cover 12 (12') and receptacle 10 (10') will be snugly held together.

Mounted on the top surface of the cover 12 (12') are two supporting members 18 (18'). Secured between the two supporting members 18 (18') is an axle 28 (28'). Rotatably secured to the axle 28 (28') is a handle 20 (20'). As shown in FIGS. 1 and 6, the supporting members 18 (18') are essentially wedge-like portions which are built up on the top surface of the cover 12 (12'). In the preferred embodiments, they can be made integral with the cover 12 (12'). Any other suitable supporting member may be substituted, as long as they afford support for the handle 20 (20'). If desired, instead of using the axle 28 (28'), each side of the handle may be secured in a respective supporting member by means of a nut and bolt. In such an arrangement, washers may be provided to facilitate rotation of the handle. As long as the handle is rotatably mounted on the cover, any other suitable arrangement for its supports may be provided. As is clearly shown in FIGS. 2 and 7, for example, the handle 20 (20') includes a gripping portion 22 (22'). This portion is preferably elongated to provide a sufficient gripping surface for the operator of the device.

An operating opening 34 (34') is provided in the top surface of the cover 12 (12'). The size of the opening 34 (34') is dependent on the size of the nub portion 36 (36') of the syringe 38 (38'). In the preferred embodiments, as is shown in FIGS. 2 and 7, the operating opening 34 (34') has a shoulder 42 (42') which is shaped so that a contoured portion 44 (44') of the syringe 38 (38') will rest securely within the operating opening 34 (34'). It must be appreciated that the shoulder portion 42 (42') need not correspond in shape to the contoured portion 44 (44') of all syringes. Certain sized syringes may rock to a certain extent within the operating opening, but this will not be detrimental to the operation of the device. The only requirement is that the operating opening 34 (34') be sufficiently large for passage of the nub portion 36 (36'). Extending beyond the nub 36 (36') is the needle portion 40 (40') of the syringe 38 (38'). As is shown in FIGS. 2 and 7, the needle 40 (40') extends quite far into the inner region 46 (46') of the receptacle 10 (10').

Referring now to FIGS. 1-4, the first embodiment of the invention is illustrated. In addition to the above components, which are common to all of the embodiments, two coaxially arranged gears 24 are provided on the inner end 30 of the handle. As shown in FIG. 2, the gears 24 are made integral with the gripping portion 22 of the handle. Other embodiments are also possible, so long as the gears 24 are rotated when the handle is moved up and down. In assembling the device of the instant invention, the axle 28 is passed through central apertures in the gears 24. As arranged in the preferred embodiment, each of the gears 24 is disposed alongside a respective supporting member. A support plate 48 is secured to the underside 13 of the cover 12 by rivets or bolts 50 or other suitable means, such as adhesives.

Movably positioned within the supporting plate is a rack 52 with a plurality of teeth 54. The teeth 54 should be disposed beneath an opening 56 in the top surface 11 of the cover 12. Further, the rack should be positioned so that the teeth 54 of the rack 52 are engageable with the teeth 26 on the gears 24. In the preferred embodiment, the rack 52 has two sides 56, each with a plurality of teeth 54. The teeth 54 on each of these sides 56 interact with the teeth 26 on a respective gear 24. Thus, by rotating the handle and, consequently, the gear 24, translational motion of the rack 52 is effected. Secured to the rack 52 is a cutting block or means 58. The cutting block 58 includes a supporting portion 60 on which a lower blade or cutting surface 62 and an upper blade or cutting surface 64 are positioned. In the preferred embodiments, the rack 52 can be made integral with the top surface of the supporting portion 60. In some embodiments, it may be desirable for the upper blade 64 to be made integral with a distal end of the rack 52.

The lower blade 62 is designed to cut off the needle 40 of the syringe 38 and is appropriately shaped. Cutting off of the nub 36 is accomplished by the upper blade 64, and that blade is appropriately shaped for that purpose. Any blades which will accomplish these cutting operations may be used in the device of this invention. As shown in FIG. 3, the upper cutting surface or blade 64 may have its outer end 65 cut off at an angle in order to form a relatively sharp surface. The distal end 63 of the lower blade or cutting surface 62 may have a substantially rectangular or square cross-section. Because it is cutting off the needle portion, it does not necessarily have to be sharp. If desired, a support structure may be included in order to offer resistance to the upper and lower blades. Thus, when the upper and lower blades push the nub and needle portions against the support structure, the resistance of the support structure will assist in cutting off the nub and needle portions.

Figure 5:
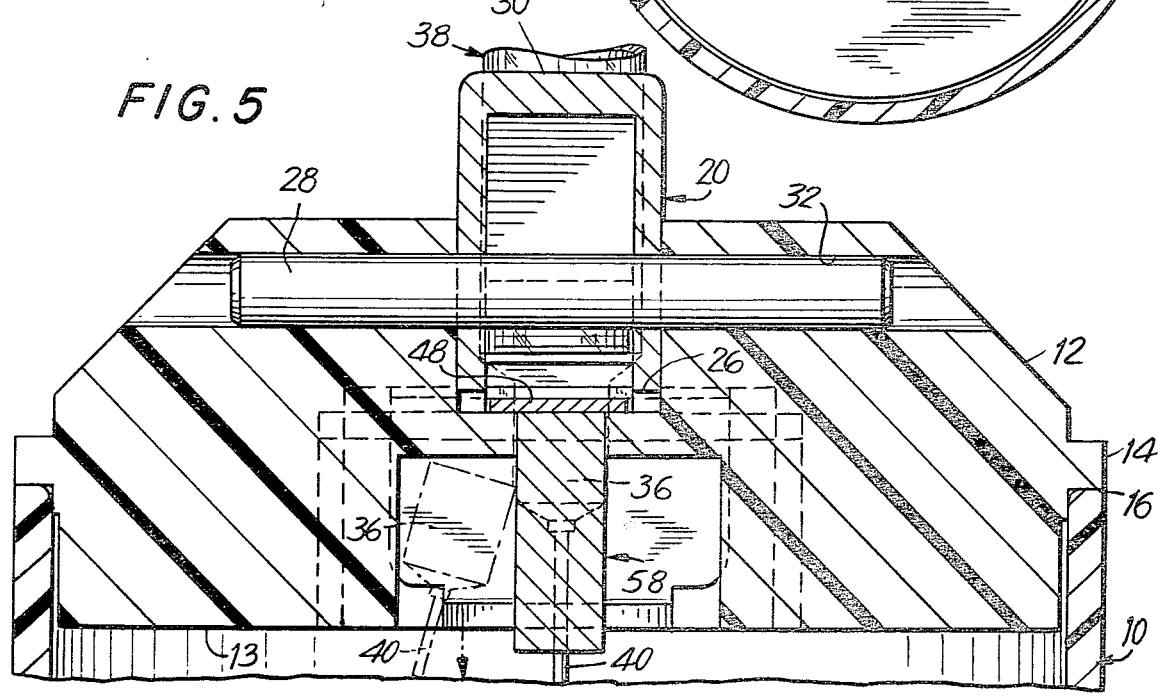
FIG. 5 is a cross-sectional view taken substantially along the line 5—5 of FIG. 2, showing the hypodermic needle and the nub portion in position for destruction, and showing in phantom the cutoff nub of the syringe.
Figure 8:
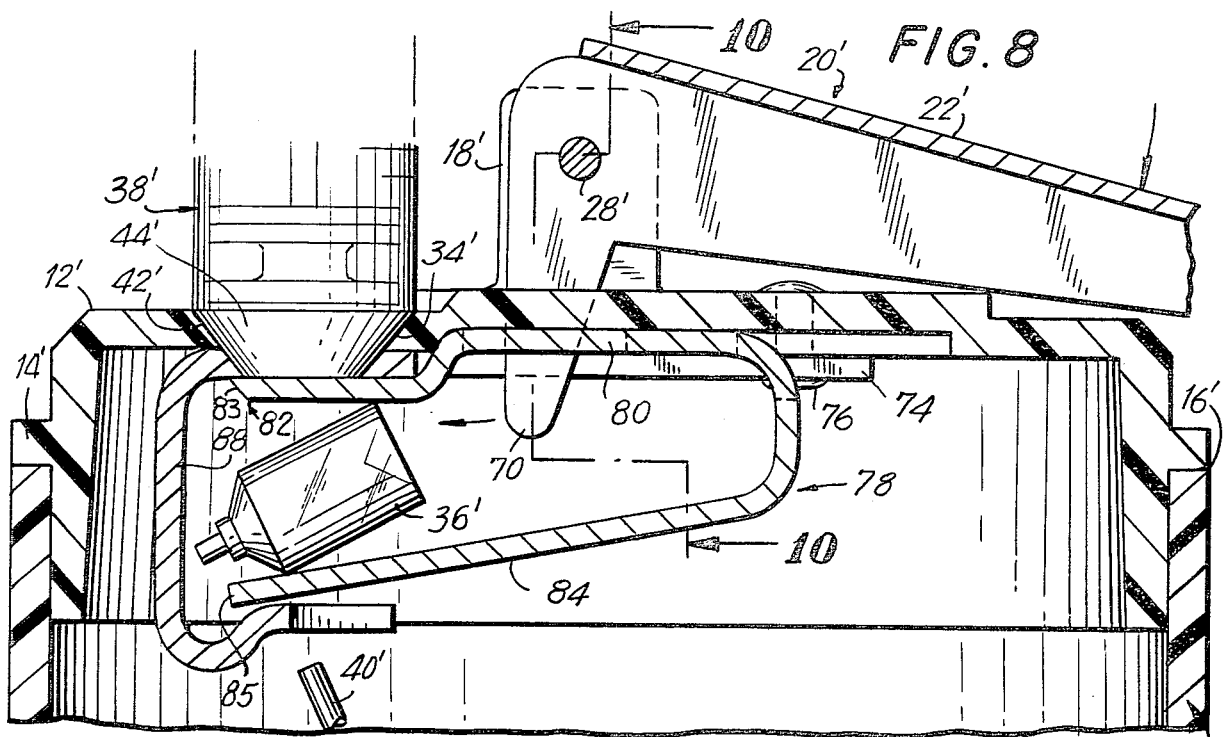
FIG. 8 is a view similar to FIG. 7, but showing the positioning of the device after the needle and nub portions have been cut off.

In operation, the syringe 38 is positioned in the device, so that the contoured portion 44 rests on the shoulder 42 of the operating opening 34. In this position the nub 36 and the needle 40 extend downward into the inner region 46 of the receptacle 10 (See FIG. 2). The handle 20 in its initial position has the outer end 66 of its gripping portion 22 positioned furthest away from the top surface 11 of the cover 12. Further, the rack 52 and the blades 62 and 64 are in their inoperative position, in this case the left most position, as seen in FIG. 2. By moving the gripping portion 22 of the handle downward, towards the upper surface 11 of the cover, the teeth 26 of the gears 24 will necessarily come into engagement with the teeth 54 of the rack 52 (see FIG. 3). Thus, the rack will be caused to move towards the right, as will the lower and upper blades 62 and 64. Since the nub 36 and the needle 40 are in the path of the blades 64 and 62, they will necessarily be cut off by these blades (see FIGS. 3 and 5). The cutoff needle and nub portions will then drop to the interior region 46 of the receptacle 10. Therefore, by such means, the effective useful life of the syringe and needle has been terminated.

Referring now to FIGS. 6–10, a second embodiment of the invention is illustrated. As was true of the above description of the first embodiment, the second embodiment includes the common elements of the invention, such as the receptacle, the cover and the handle.

Included on an inner end 68 of the handle 20' is a projection 70. The projection 70 extends substantially downward or at a right angle to the axis of the handle 20' and extends through an opening 72 in the top surface 11' of the cover 12' into the inner region 46' of the receptacle 10'. If desired, the handle may be provided with a single projection that is located in a central portion of the inner end 68 of the handle. Further, it is possible to provide the handle with a projection 70 extending downward from each side face of the inner end 68. Either construction may be used and neither has any advantage over the other.

Figure 9:
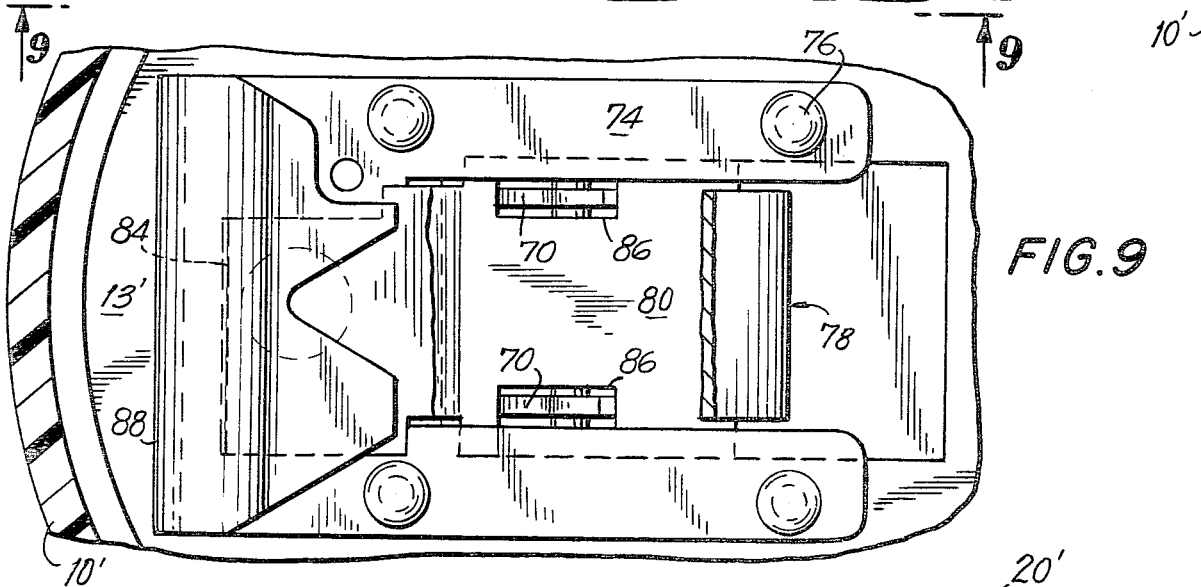
FIG. 9 is essentially a bottom plan view of the cover of the device, taken substantially along the line 9—9 of FIG. 8.
Figure 10:
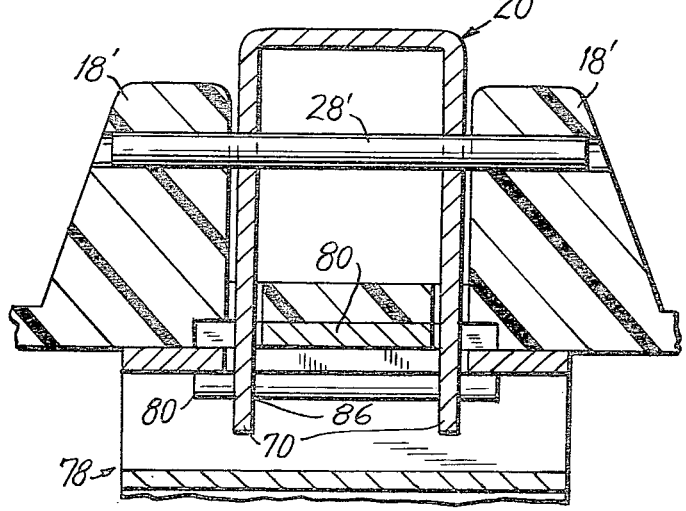
FIG. 10 is a cross-sectional view taken substantially along the line 10—10 of FIG. 8, and showing the manner in which the handle is mounted on the cover.

Positioned on the undersurface 13' of the cover 12' is a supporting plate 74 (see FIG. 9). Bolts 76, or other suitable means, may be used to attach the supporting plate 74 to the cover 12'. Movably positioned with respect to the supporting plate 74 is a cutting or severing device 78. The cutting device 78 is essentially U-shaped and includes a top portion 80 movably positioned between the supporting plate 74 and the undersurface 13' of the cover 12'. The top portion 80 also includes an upper blade or cutting surface 82, and a bottom portion of the cutting device 78 includes a lower blade of cutting surface 84.

The upper and lower blades 82 and 84 are shaped to cut off the nub portion 36' of the syringe and the needle 40' and may be made of any material which is suitable for such blades. As shown in FIG. 7, it is preferred that the upper blade or cutting surface 82 be provided with a relatively sharp, knife-like edge portion 83. The sharpness of the edge 83 should be such that the upper blade 82 will be able to cut through the plastic portion 36' of the syringe. The cutting edge 85 of the lower blade or cutting surface 84 may have an essentially rectangular or square cross-section. This surface need only be sufficiently sharp to cut off the metal needle portion 40' of the syringe.

Aligned with the opening 72 in the top 11' of the cover 12' are openings 86 made in the top portion 80 of the cutting device 78. As is most clearly shown in FIG. 7, the projections 70 of the handle 20' are positioned so that they will pass through respective openings 86. By such means, movement or rotation of the handle and, necessarily, the projection 70 will cause translational movement of the cutting device 78 in a horizontal plane.

In operation, the syringe 38' is secured in the device, so that the contoured portion 44' rests on the shoulder 42' of the operating opening 34'. In this position the nub 36' and the needle 40' extend downward into the inner region 46' of the receptacle 10 (see FiG. 7). The handle 20' in its initial position has the outer end 66' of its gripping portion 22' positioned furthest away from the top surface of 11' of the cover 12. Further, the cutting device 78, including the upper and lower blades 82 and 84, is in its inoperative position, in this case the right most position (FIG. 7). By rotating or moving the gripping portion 22' of the handle downward, towards the upper surface 11' of the cover, the projections 70 of the handle necessarily cause translational movement of the cutting device 78. Therefore, the cutting device will be caused to move towards the left, as will the upper and lower blades 82 and 84. Since the nub portion 36' and the needle 40' are in the path of the blades 82 and 84, they will necessarily be cut off by these blades (see FIG. 8). The severed needle and nub portions will then drop to the interior region 46' of the receptacle 10'. By such means, the syringe and needle are rendered effectively useless.

If desired, a limit means 88 may be included. Such a means can serve any one of several purposes. It can be used to restrict the motion of the upper and lower blades. In addition, it can be used to offer resistance against the blades in order to assist in the cutting off or severing of the nub and needle portion. Lastly, it can be used to direct the nub portion into the interior region of the device.

In the case where there is a single projection 70 intermediate the inner end 68 of the handle, a single opening 86 may be provided in a central region of the top portion 80 of the cutting device 78. In all other respects, the device would work the same as the device described above.

The above described embodiments are only two of the many ways that may be used to mechanically link the handle and the upper and lower blades. Any device which mechanically links the handle and the upper and lower blades, so that actuation or movement of the handle will cause simultaneous cutting off or severance of the nub and needle portions of the syringe, is intended to come within the scope of this invention.

Moreover, it is possible to construct the invention without a receptacle or cover. The barest bones of the invention include some device for orienting the nub portion of the syringe and the needle in a first plane; some severing device which operates in a plane perpendicular to the first plane; and a device for moving the severing means so that it will simultaneously cutoff or severe both the nub portion and the needle portion of the syringe. Moreover, if desired, the entire invention can be set in a horizontal plane, i.e. the needle and syringe are oriented in a horizontal plane and the severing means moves in a vertical plane. Though these other embodiments of the invention are not specifically illustrated or described in this application, it is believed that they come within the scope of this invention.

I claim:

1. A syringe and needle destroyer comprising:
a receptacle into which a distal end portion of said syringe and said needle drop after being severed;
a base including a cover fitted onto said receptacle;
means positioned on said base for orienting said distal end portion of said syringe and said needle in a plain perpendicular to a plane of said base, said means for orienting including said cover and said cover having an operating opening and a shoulder portion, a middle portion of said syringe resting on said shoulder portion, and said distal end portion of said syringe and said needle passing through said operating opening and being suspended within said receptacle;
severing means movably mounted on said base on an underside of said cover and movable in a horizontal plane parallel to said plane of said base for severing both said distal end of said syringe and said needle;
a handle movably mounted on said cover of said base for rotation about an inner end of said handle; and
means for mechanically linking said handle and said severing means, such that movement of said handle in a plane perpendicular to said plane of said base causes movement of said severing means, said means for mechanically linking including at least one projection positioned on said inner end of said handle and at a right angle to an axis of said handle, extending through an opening in said cover, and cooperating with a respective opening in said severing means.

2. A syringe and needle destroyer comprising:

a receptacle into which a distal end portion of said syringe and said needle drop after being servered;

a base including a cover fitted onto said receptacle;

means positioned on said base for orienting said distal end of portion of said syringe and said needle in a plain perpendicular to a plane of said base, said means for orienting including said cover and said cover having an operating opening and a shoulder portion, a middle portion of said syringe resting on said shoulder portion, and said distal end portion of said syringe and said needle passing through said operating opening and being suspended within said receptacle;

severing means movably mounted on said base on an underside of said cover and movable in a horizontal plane parallel to said plane of said base for severing both said distal end of said syringe and said needle;

a handle movably mounted on said cover of said base for rotation about an inner end of said handle; and means for mechanically linking said handle and said severing means, such that movement of said handle in a plane perpendicular to said plane of said base causes movement of said severing means, said means for mechanically linking including gear means on said inner end of said handle, and rack means on said severing means, teeth of said rack means meshing with teeth of said gear means.

3. A syringe and needle destroyer according to either of claims 1 or 2, wherein said severing means includes first and second cutting surfaces for respectively severing said distal end portion of said syringe and said needle.

* * * * *